United States Patent [19]
Nakamura et al.

[11] Patent Number: 5,220,098
[45] Date of Patent: Jun. 15, 1993

[54] PROCESS FOR SEPARATING 2,7-DIMETHYLNAPHTHALENE UNDER PRESSURE

[75] Inventors: Kazumoto Nakamura; Shinji Aihara, both of Tokyo; Yutaka Mito, Hyogo; Masami Takao, Hyogo; Hitoshi Hatakeyama, Hyogo, all of Japan

[73] Assignees: Petroleum Energy Center; Showa Shell Sekiyu Kabushiki Kaisha, both of Tokyo; Kobe Steel Limited, Hyogo, all of Japan

[21] Appl. No.: 756,792

[22] Filed: Sep. 9, 1991

[30] Foreign Application Priority Data

Sep. 12, 1990 [JP] Japan .................................. 2-239984

[51] Int. Cl.$^5$ .............................................. C07C 7/14
[52] U.S. Cl. .................................................. 585/812
[58] Field of Search ...................................... 585/812

[56] References Cited
U.S. PATENT DOCUMENTS 3,202,726 8/1965 Malmberg et al. .................. 585/812
3,590,091 6/1971 Skarada et al. ..................... 585/812

Primary Examiner—Asok Pal
Assistant Examiner—Nhat D. Phan
Attorney, Agent, or Firm—Cushman, Darby & Cushman

[57] ABSTRACT

The present invention relates to a process for separating 2,7-DMN, characterized in that a mixture containing at least 50% by weight of 2,7-DMN and the other DMN isomers obtained by preliminarily concentrating a fraction in the range of 250°–270° C. of catalytically cracked petroleum oil is preliminarily adjusted to a temperature of 60°–90° C. to form a slurry containing the crystal of 2,7-DMN, which is placed in a tightly sealed pressure vessel, adiabatically pressurized to the range of 500–2,500 kgf/cm$^2$ and solidified to form a state of co-existing of solid and liquid phases, liquid is then discharged under pressure from the solid-liquid co-existing system, the solid remaining in the vessel is pressed to discharge the liquid remaining between the solid particles, which are integrated to give 2,7-DMN having a purity of 98% by weight or more.

3 Claims, 2 Drawing Sheets

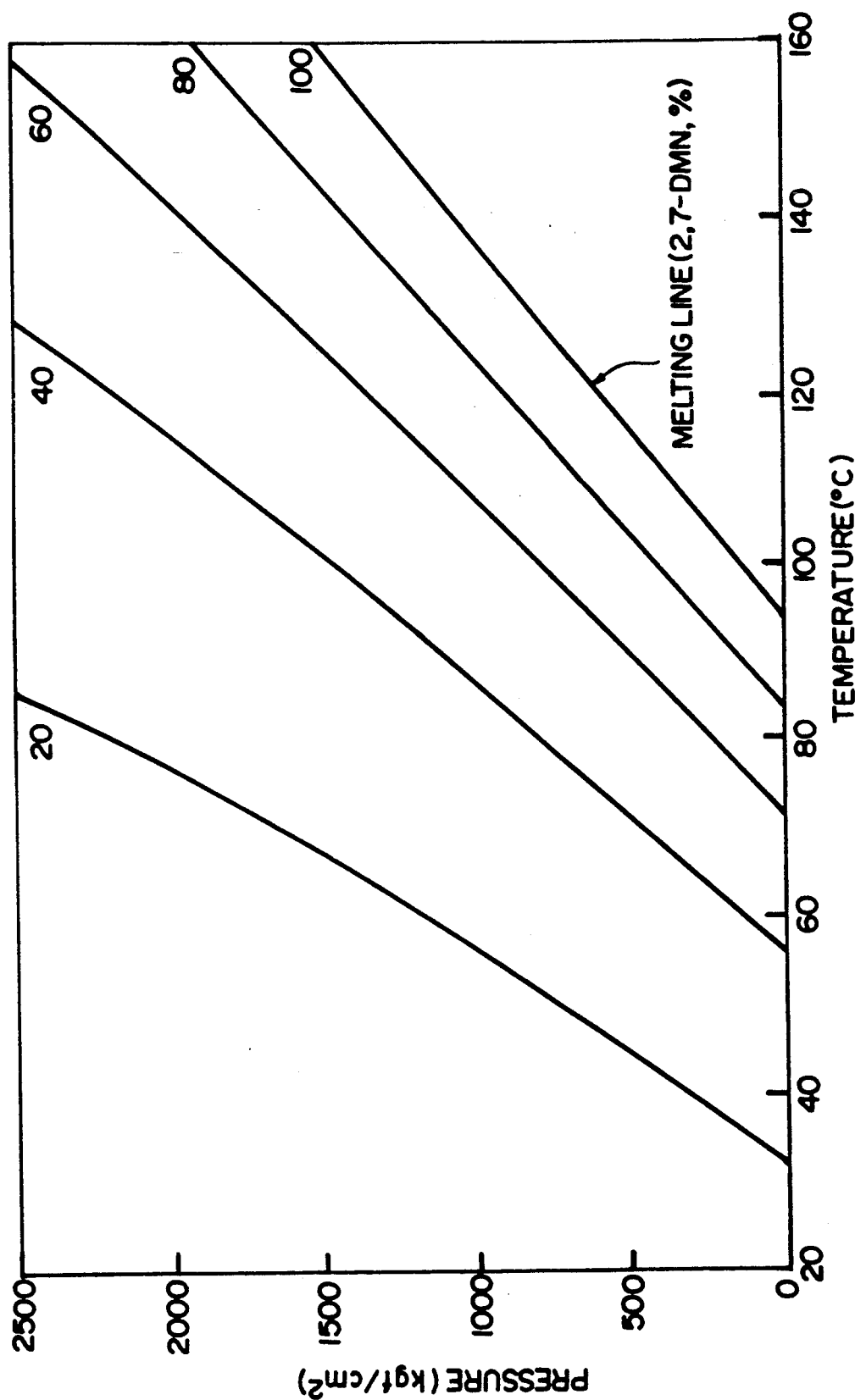

PROCESS FOR SEPARATING 2,7-DIMETHYLNAPHTHALENE UNDER PRESSURE

FIELD OF THE INVENTION

The present invention relates to a process for separating and obtaining 2,7-dimethylnaphthalene at a purity greater than 98 wt % from a mixture of which contains dimethylnaphthalenes.

BACKGROUND OF THE INVENTION 2,7-DMN is oxidized to produce naphthalene 2,7-dicarboxylic acid, which is an industrially important material for manufacturing polyesters. 2,7-DMN is contained in various fractions of petroleum or coal tar as mixtures together with other DMN isomers.

There have hitherto been proposed several methods for separating 2,7-DMN from these fractions.

For example, one of the proposed methods involves concentrating and extracting a DMN fraction from a raw material, such as petroleum or coal tar, using suitable techniques, such as fractionation; cooling the DMN; concentrate to remove, i.e. crystalize out, a portion of 2,6-DMN; treating the remaining DMN mixture which contains the 2,6- and 2,7- isomers in the ratio of their eutectic mixture with a zeolite adsorbent to selectively adsorb the 2,7-DMN; and isolating the 2,7-DMN by subjecting the adsorbed material to a desorption treatment. The conventional crystallization method, however, does not yield 2,7-DMN having a sufficiently significantly high purity because, although the DMN mixture is rich in 2,7-DMN, it still contains 2,6-DMN having sufficiently high melting point, and thus the crystallization method only yields a eutectic mixture.

As described above, various fractions of petroleum or coal tar contain substantially equivalent amounts of 2,7-DMN and 2,6-DMN and many additional components such as, for example, the other DMN isomers.

2,7-DMN and 2,6-DMN have melting points which are very close to each other. Thus, even with conventional separation techniques, these isomers tend to form eutectic mixtures for solid solutions.

There are other problems associated with the conventional techniques for separating 2,7-DMN from a mixture of dimethylnaphthalenes. For example, there are generally lower recoveries of 2,7-DMN than are desired. In addition, the purity of the 2,7-DMN which is isolated, is somewhat lower than desired, and the purity can be increased only with great difficulty and at excessively high costs through further or alternative separation and purification procedures.

SUMMARY OF THE INVENTION

The present invention relates to a process for separating 2,7-DMN, characterized in that a mixture containing at least 50% by weight of 2,7-DMN and less than 50% of other DMN isomers, which is obtained by preliminarily concentrating a fraction in the range of 250°–270° C. of catalytically cracked petroleum oil, is preliminarily adjusted to a temperature of 60°–90° C. to form a slurry containing the 2,7-DMN, which is placed in a tightly sealed pressure vessel, adiabatically pressurized to the range of 500–2500 kgf/cm$^2$ and solidified to form a state of co-existing of solid and liquid phases, liquid is then discharged under pressure from the solid-liquid co-existing system, the solid remaining in the vessel is pressed to discharge the liquid remaining between the solid particles, which are integrated to give 2,7-DMN having a purity of 98% by weight or more.

BRIEF DESCRIPTION OF THE DRAWINGS

In the accompanying drawings,

FIG. 2 is a diagrammatic illustration of an apparatus for practicing the process of the present invention and FIG. 3 is a graphical illustration of solid-liquid equilibrium curve of 2,7-DMN by temperature and pressure.

DETAILED DESCRIPTION OF THE INVENTION

Figure 1:
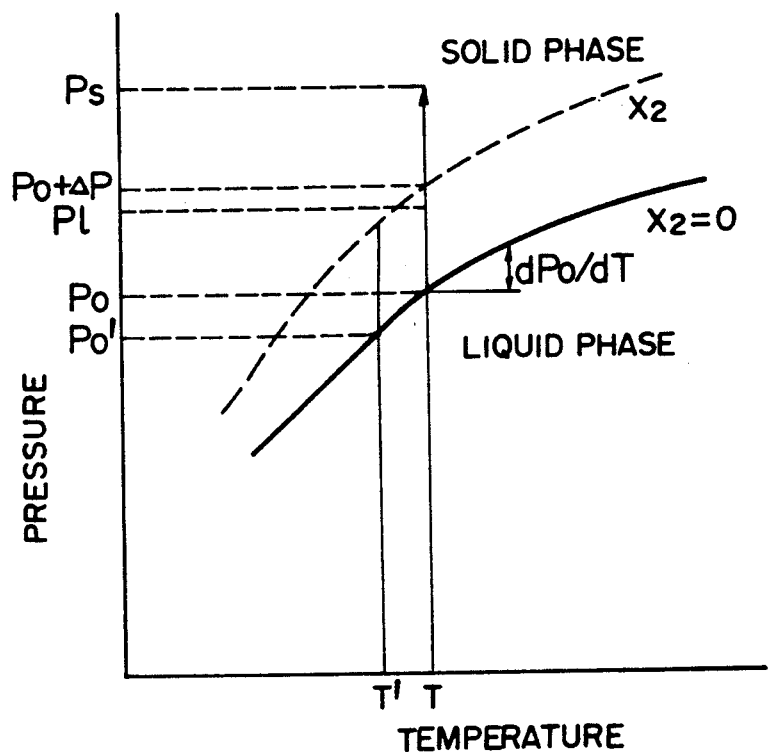
FIG. 1 is a graphical illustration of a solid-liquid equilibrium curve of a substance by temperature and pressure for explaining the high pressure crystallization method.

The present invention relates to a process for separating 2,7-dimethylnaphthalene from a mixture containing at least 50% by weight of 2,7-dimethylnaphthalene and other dimethylnaphthalene isomers. The method involves preliminary adjusting the temperature of the mixture to 60°–90° C. to obtain a slurry, which slurry contains crystals 2,7-dimethylnaphthalenes; injecting the slurry into a high pressure vessel for conducting a high pressure crystallizaton; adiabatically pressurizing the vessel to a pressure of 500–2,500 kgf/cm$^2$ to increase the quantity, i.e. amount, of 2,7-dimethylnaphthalene crystals whereby coexistence of solid-liquid phases exist at the high pressure condition; discharging the liquid phase component from the high pressure vessel, the discharging being conducted under pressure, to increase the ratio of the solid phase relative to the liquid phase within the vessel; lowering the pressure of the residual liquid phase so as to, dissolve partially and purify the solid phase; discharging the residual liquid phase by applying pressure to the solid phase within the high pressure vessel whereby 2,7-dimethylnaphthalene crystal block having a purity of at ≧98% by weight is obtained within the high pressure vessel.

The present process includes a further embodiment wherein the high pressure crystallization step, the separation of the solid and liquid is initiated at a pressure in the range of 500–2000 kgf/cm$^2$, and the temperature in the initiation phase is in the range of 70°–120° C.

The high pressure crystallization is described in "The method for isolating and purifying substances" (Japanese Patent Publication No. 41282/1981).

Briefly summarized, in this method a liquid mixture containing two or more substances is pressurized, and a certain substance in the mixture is solidified and separated from the residual liquid by the effect of the pressure. In other words, this method involves separating and purifying technique wherein a liquid mixture containing two or more substances is placed in a tightly sealed pressure vessel, a portion of the desired substance, 2,7-dimethylnaphthalene, is solidified to form a solid-liquid co-existing state, the liquid is discharged from the co-existing system while maintaining the pressure of the solid-liquid co-existing system at a higher level than equilibrium pressure of the objective stabstance, then the solid remaining in the vessel is pressed for discharging the residual liquid between the solid particles and integrating the solid particles.

Referring to the aforementioned phenomenon on the basis of the thermodynamics of solutions, there is the following equation when $X_2$ is a relatively small value:

$$\Delta P = \frac{RT}{\Delta V} X_2$$

wherein

ΔP (kg/cm$^2$): difference between $P_1$ and $P_0$ where $P_1$ (kg/cm$^2$): equilibrium pressure between liquid crystal; $P_0$ (kg/cm$^2$): a solid-liquid critical pressure of a pure substance,
R: the gas constant,
T (°K): a treating temperature,
ΔV: a volume change per mole of solidification (generally negative but the cases of water-water system),
$X_2$ (mol): concentration of impurity in the residual liquid.

2,7-dimethylnaphthalene is separated most effectively, if there is a relation $$P_0 < P_L < P_0 + \Delta P < P_3,$$

where
$P_0$ and ΔP are defined above,
$P_3$ (kg/cm$^2$): contact pressure on the surface of the crystal particles,
$P_0 + \Delta P$ (kg/cm$^2$): the solid-liquid equilibrium pressure,
$P_L$ (kg/cm$^2$): discharged pressure of the residual liquid.

An amount of solid recovered increases but the purification effect decreases as $P_L$ becomes closer to $P_0 + \Delta P$. Contrariwise, when $P_L$ becomes closer to $P_0$, the recovering effect decreases slightly while the purification effect increases. An increased amount of a solid of high purity is obtained by merely isolating a relatively small amount of the residual liquid when $P_L$ is made closer to $P_0$ rather than $P_0 + \Delta P$ corresponding to the concentrations and the discharged amount of the residual liquid.

The present invention will now described in greater detail with reference to the drawings.

Referring to FIG. 1, the gradient of the solid-liquid equilibrium line of a substance $dP_0/dT$ is generally larger than zero. A pure substance, that is a substance having an impurity concentration = 0, reaches the solid-liquid equilibrium at a pressure $P_0$ at a temperature T. When the impurity concentration is $X_2$, the pressure at the solid-liquid equilibrium is $P_0 + \Delta P$. If the discharge pressure is set at $P_L$, solid in the neighborhood of a liquid having an impurity concentration $X_2$ is melted, so that the solid-liquid equilibrium can be maintained at $P_L$ and a higher purity can be realized. At this time, the statistic mean pressure $P_3$ at the contact surface of crystal particles is high far from these values, and thus pressing force is applied to the crystal particles and produces a so-called "squeezing out" state of the residual liquid between the particles.

In the figure, if temperature is decreased to T' by melting of a little amount of the crystals along with the setting up of the discharging pressure $P_L$, $P_0'$ may be again defined as $P_0$ for adjusting the discharging pressure or may be understood as a variable which returns to the original value along with the recovery of the temperature.

Figure 2:
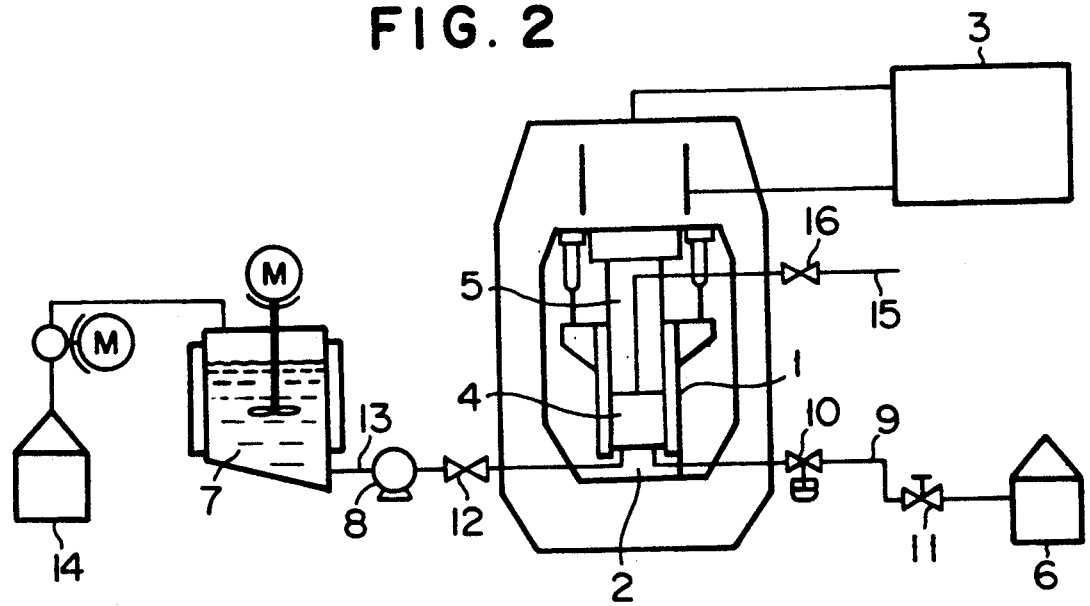

In FIG. 2, a pressure vessel 1 is provided with a bottom cap 2 at a lower part, and a piston 5 is provided so that it is reciprocated vertically within the vessel 1 by the operation of a hydraulic device 3. A crystallization chamber 4 is formed by the piston 5 and the bottom cap 2 within the pressure vessel 1. The crystallization chamber 4 and discharged liquid tank 6 are connected through a pressure decreasing mechanism 10 and a value 11 by a pipe line 9. The crystallization chamber 4 and a preliminary crystallization vessel 7 are connected to each other through a raw material supplying pump 8 and a valve 12 by a pipe line 13.

In this apparatus, the raw material is supplied from the raw material tank 14 to the preliminary crystallization vessel 7, where the material is cooled and crystallized to form seed crystals for high pressure crystallization. Such a procedure is carried out because the high pressure crystallization of a liquid free of seed crystals requires a high pressure for forming an initial crystal and super fine crystals may be formed due to the formation of crystals under an excessive supersaturation condition by a rapid pressurization, so that separation of solid and liquid becomes difficult. When the raw material is supplied in the state of slurry containing seed crystals, such supersaturation will not occur and growth of crystals is initiated along with the pressurization.

The raw material is next injected into the crystallization chamber 4 through the valve 12 from the pipe line 13. When the raw material is filled within the crystallization chamber 4, the overflow of the liquid starts through the overflow pipe 15 having an opening at the top of the piston, and thus the valves 12 and 16 are closed on the detection of the overflow to initiate pressurization by the piston 5. If the raw material liquid is pressurized, the crystallization of a specific substance in the raw material progresses to realize a solid-liquid co-existing state under a high pressure within the crystallization chamber 4. The solid generated at this time is generally a substance having an extremely high purity. In this connection, temperature within the crystallization chamber 4 is increased by the latent heat of solidification generated with the progression of solidification. However, in the high pressure crystallization process, preventing a temperature increase via a cooling technique is generally not carried out, and an adiabatically pressurizing method is employed. Temperature reached by increasing pressure, that is the temprature of initiating the separation of solid and liquid, influences the purity and recovery of the product, and thus it is adjusted by a temperature of a supplied liquid in consideration of the specific heat or the latent heat for solidification of the raw material.

When pressurization is conducted up to a certain level and a certain ratio of solid and liquid is realized, the valve 11 is opened while the pressure acting from the hydraulic device 3 on the piston 5 is maintained and the pressure within the crystallization chamber 4 is maintained, and the liquid within the crystallization chamber 4 is discharged through the pressure decreasing mechanism 10 into the discharge tank 6. When the piston is further lowered while the pressure applied to the piston 5 maintained, the crystal particle groups within the crystallization chamber 4 are pressurized and pressed and the residual liquid between the crystal particle groups is subjected to the so-called "squeezing-out action" and discharged into the discharge tank 6.

When the piston 5 is further lowered, the crystal particle groups is formed into a large block with the profile of the crystallization chamber 4. When the liquid is substantially separated from the solid, the pressure of the liquid phase between the crystal particles within the crystallization chamber 4 is gradually decreased, so that the surface of the crystal particles are melted partially and the so-called "sweating washing" is carried out to purify the solid product. When the pressure of the discharge from the crystallization chamber is decreased to a certain pressure, the lowering of the piston 5 is stopped, the rising of the piston is initiated and the high pressure vessel 1 is also raised, the solid product can be removed from the vessel 1 in the state that the product is put on the bottom cap 2. The product is removed by a removing device (not shown in the figure), the high pressure vessel 1 is lowered and fitted with the bottom cap 2, and then the similar process is repeated from the raw material injecting step. In addition, residual liquid in the overflow pipe is purged by an inert gas to the product such as nitrogen gas to prepare for detecting the full liquid on injection in the following step.

Preparation of suitable raw materials for conducting the present process may be described as follows.

In order to conduct the high pressure crystallization of the present invention, a mixture of 2,7-DMN and other DMN isomers which contains at least 50% by weight of 2,7-DMN or more, preferably 70% by weight or more of 2,7-DMN as the raw material is used.

It is because 2,7-DMN is poorly recovered when 2,7-DMN in the raw material has a content of 50% by weight or less. In such cases, 2,7-DMN cannot be obtained in the purity of 98% by weight or more.

The raw material for conducting the pressure crystallization contains 2,7-DMN of at least 50% by weight or more, preferably 70% by weight or more.

In order to prepare DMN isomers containing at least 50% by weight or more of 2,7-DMN as raw material used in the process of the present invention, various methods, for example, described in Japanese Patent Publication No. 45863/1974 (separation by crystallization of a hydrogenated product), Japanese Patent Laid-Open Pubilication No. 35368/1974 (complex formation), U.S. Pat. No. 3,668,267 (Zeolite method) and U.S. Pat. No. 3,235,615 (cooling crystallization method) can be used in combination thereof.

A typical method is described as follows. Fractions having a boiling point of a catalytically cracked petroleum oil in the range of 250°–270° C., preferably 257°–265° C. are used as a starting raw material. The fractions are cooled to a cooling temperature of −30° C. to −10° C. according to the cooling crystallization method to crystallize and remove 2,6-DMN. The DMN mixture from which 2,6-DMN has been removed is treated with Na-Y Zeolite according to the Zeolite method at a temperature of 80°–100° C. under the condition of SV1-10 g/g/hr and further treated at a cooling crystallization temperature of −30° C. to 30° C. according to the cooling crystallization method.

In this connection, the raw material is preferably supplied in a state of slurry as described above in the high pressure crystallization method, so that the raw material employed in the present invention is preferably formed into a slurry which contains solid in a ratio of about 5-25% by preliminarily cooling the raw material to a temperature of about 50°–90° C.

The temperature at which the raw material is supplied has also an intimate relationship to the purity and yield of the product. When the raw material is supplied at a temperature of 50° C. or less, the purity is lowered due to the insufficient sweating washing and insufficient squeezing at the reduced pressure. On the other hand, if the raw material is supplied at a temperature of 90° C. or more, the process is not economical because the the yield is lowered notwithstanding the improvement of the purity.

The present invention is illustrated with reference to Examples and Comparative Examples, but it should not be construed to be limited thereto.

EXAMPLE

A raw material mixture (D) comprising mainly DMN isomers such as a mixture containing 75.7% of 2,7-DMN and 10.1% of 2,6-DMN was adjusted to a temperature of 100° C. to form a slurry containing the crystal of 2,7-DMN, supplied to a high pressure vessel having a piston/cylinder structure as shown in FIG. 2 and pressurized adiabatically at pressure of 800 kgf/cm$^2$ (case E-1), 1,000 kgf/cm$^2$ (case E-2) and 1,500 kgf/cm$^2$ (case E-3) by the oil pressure acting on the piston. While the oil pressure acting on the piston was maintained, the liquid phase within the high pressure vessel was discharged, and the crystal was squeezed until the pressure of the liquid phase was lowered to 200 kgf/cm$^2$ (case E-1), 400 kgf/cm$^2$ (case E-2) and 450 kgf/cm$^2$ (case E-3).

The temperature of the raw material supplied and the pressure of the high pressure crystallization were obtained from the melting latent heat of 2,7-DMN and the specific heat of the raw material mixture.

The purities and yields of the products obtained in respective cases E-1, E-2 and E-3 are shown in Table 1.

TABLE 1

| Composition | D | E-1 | E-2 | E-3 |
|---|---|---|---|---|
| Purity of 2,7-DMN (% by weight) | 75.7 | 100 | 98.5 | 98.1 |
| Purity of 2,6-DMN (% by weight) | 10.1 | 0 | 1.1 | 1.1 |
| Yield of 2,7-DMN (%) | — | 47.6 | 46.8 | 41.5 |

Effect of the Invention

The following effects are obtained by the present invention.

1) The whole system can be controlled under a uniform condition because of the pressure control instead of temperature control and the purity of 2,7-DMN can be increased, so that a high recovery and a high purification efficiency can be obtained.

2) The residual mother liquid can be used repeatedly at the next process cycle and thus causes no problems.

3) The apparatus is compact in size and inexpensive in purification cost.

4) Both batchwise and continuous methods can be done and the time required therefor is short.

We claim:

1. A process for separating 2,7-dimethylnaphthalene consisting essentially of:
    (a) providing a mixture containing at least 50% by weight of 2,7 dimethylnaphthalene and at most 50% by weight of other dimethylnaphthalene isomers;
    (b) preliminarily adjusting the temperature of said mixture to 60°–90° C. to form a slurry containing crystals of 2,7-dimethylnaphthalene,
    (c) injecting said slurry into a high pressure vessel for conducting a high pressure crystallization,
    (d) adiabatically pressurizing the vessel to a pressure of 500–2,500 kgf/cm$^2$ to increase the amount of crystals of 2,7-dimethylnaphthalene whereby solid and liquid phases co-exist, (e) discharging the liquid phase from the pressurized vessel whereby an increased ratio of the solid phase relative to a residual liquid phase within the vessel is obtained, (f) lowering the pressure within the pressurized vessel whereby the solid phase is purified and partially dissolved in the residual liquid phase, (g) applying pressure on said solid phase so that the residual liquid phase is separated from the solid phase, and discharging the thus separated liquid phase from the vessel whereby 2,7-dimethylnaphthalene crystals having a purity of 98% by weight or more are obtained.

2. A process according to claim 1, wherein step (e) the initial pressure in the separation of the solid and the liquid phases is in the range of 500–2,000 kg/cm$^2$ and the initial temperature is in the range of 70°–120° C.

3. A process for separating 2,7-dimethylnaphthalenes from a dimethylnaphthalene mixture comprising:

adjusting the temperature of a dimethylnaphthalene mixture containing at least 50% by weight of 2,7-dimethylnaphthalene and at most 50% by weight of other dimethylnaphthalene isomers to 60°–90° C. to obtain a slurry containing 2,7-dimethylnaphthalene crystals, introducing said slurry into a high pressure vessel, adiabatically pressurizing the high pressure vessel to a pressure of 500–2,500 kgf/cm$^2$ such that the amount of 2,7-dimethylnaphthalene crystals increases, and solid and liquid phases co-exist at said pressure, discharging, while under pressure, the liquid phase from the high pressure vessel whereby the ratio of the solid phase relative to a residual liquid phase remaining within the vessel is increased, lowering the pressure applied within the vessel whereby the solid phase is purified and partially dissolves in the residual liquid phase remaining within the vessel, adjusting the pressure applied within the vessel so that the residual liquid phase is separated from the solid phase, and discharging the thus separated liquid phase from the vessel whereby 2,7-dimethylnaphthalene crystals having a purity of 98% by weight or more are obtained.

* * * * *